(12) United States Patent
Rutherford et al.

(10) Patent No.: US 11,373,247 B2
(45) Date of Patent: Jun. 28, 2022

(54) METHOD AND SYSTEM FOR MONITORING PRESCRIPTION DRUG DATA AND DETERMINING CLAIM DATA ACCURACY

(71) Applicant: HEALTHPLAN DATA SOLUTIONS LLC, Columbus, OH (US)

(72) Inventors: Gary Rutherford, Columbus, OH (US); Michael Blevins, Upper Arlington, OH (US); Jarrod Grossman, Columbus, OH (US); Douglas Bell, Denver, CO (US); Detlef Sarbok, Maineville, OH (US); Jeff Rabe, Columbus, OH (US)

(73) Assignee: HEALTHPLAN DATA SOLUTIONS LLC, Columbus, OH (US)

( * ) Notice: Subject to any disclaimer, the term of this patent is extended or adjusted under 35 U.S.C. 154(b) by 0 days.

(21) Appl. No.: 15/936,986

(22) Filed: Mar. 27, 2018

(65) Prior Publication Data
US 2019/0304021 A1    Oct. 3, 2019

(51) Int. Cl.
*G06Q 40/08* (2012.01)
*G16H 20/10* (2018.01)
*G16H 10/60* (2018.01)

(52) U.S. Cl.
CPC ............ *G06Q 40/08* (2013.01); *G16H 10/60* (2018.01); *G16H 20/10* (2018.01)

(58) Field of Classification Search
CPC .............................. G06Q 40/08; G06Q 40/00
USPC ..................................................... 705/35–45
See application file for complete search history.

(56) References Cited

U.S. PATENT DOCUMENTS

| | | | |
|---|---|---|---|
| 7,895,060 B1 * | 2/2011 | Mahoney | G06F 19/328 705/3 |
| 8,489,411 B1 * | 7/2013 | Rowe, III | G06Q 50/22 705/2 |
| 10,331,855 B1 * | 6/2019 | Bratton | G16H 40/20 |
| 10,346,358 B2 * | 7/2019 | Gorelik | G06F 16/16 |
| 2004/0054685 A1 | 3/2004 | Rahn et al. | |

(Continued)

OTHER PUBLICATIONS

International Preliminary Report on Patentability (Chapter I of the Patent Cooperation Treaty), Oct. 8, 2020, International Bureau.

*Primary Examiner* — Kirsten S Apple
(74) *Attorney, Agent, or Firm* — Meister Seelig & Fein LLP; Seth H. Ostrow, Esq.

(57) ABSTRACT

A method and system for scanning claims data, the method comprising receiving, by a computing system, contract details associated with claims, receiving, by the computer system, prescription transactions data associated with the claims, parsing, by the computer system, the transactions data into column values, and executing, by the computer system, analytics on the parsed transactions. The analytics include comparing the parsed transactions against the contract details for accurate pricing, fees, and accepted treatment protocols concerning dose and quantity, comparing the parsed transactions with independent pricing data that is based on third-party pricing data and drug information, identifying material errors in the parsed transactions, determining withholdings from payment of the claims for a portion above a tolerance level based on the identified material errors. The method further comprising presenting, by the computer system, results of the execution of the analytics to a portal.

19 Claims, 15 Drawing Sheets

(56) References Cited

U.S. PATENT DOCUMENTS

| | | | |
|---|---|---|---|
| 2007/0043595 A1* | 2/2007 | Pederson | G06Q 10/04 705/2 |
| 2007/0050209 A1* | 3/2007 | Yered | G06Q 30/04 705/2 |
| 2014/0358578 A1* | 12/2014 | Ptachcinski | G06Q 30/0201 705/2 |
| 2016/0042148 A1 | 2/2016 | Bradley | |

* cited by examiner

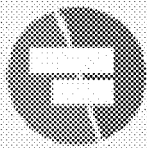

Claim Scan Overview Report

Date Range from 12/6/2016 to 9/22/2017
Batch ID | 461

| Withhold Payment Claims | | | |
|---|---|---|---|
| DAW9 Disallowed | DAW9 Disallowed | Brand dispensed; Company pay and/or copay do not meet plan design parameters | 123 | $20,377.31 |
| Retail Generic Discount | Retail Generic Discount | Price adjudicated is significantly above the contracted category pricing | 163 | $7,153.92 |
| Retail Brand Discount | Retail Brand Discount | Price adjudicated is significantly above the contracted category pricing | 471 | $6,363.80 |
| Retail Dispensing Fee | Retail Dispensing Fee | Retail Dispensing Fee significantly exceeds the contracted amount | 445 | $911.65 |
| Retail Brand Specialty | Retail Brand Specialty | Price adjudicated is significantly above the contracted category pricing | 2 | $745.60 |
| Mail Brand Specialty | Mail Brand Specialty | Price adjudicated is significantly above the contracted category pricing | 1 | $660.78 |
| Zero Balance Due Generic | Zero Balance Due Generic | Price adjudicated is significantly above the contracted category pricing | 853 | $398.25 |
| Retail Specialty Disp. Fee | Retail Specialty Disp Fee | Retail Specialty Dispensing Fee significantly exceeds the contracted amount | 0 | $336.20 |
| DAW4 Disallowed | DAW4 Disallowed | Brand dispensed; Company pay and/or copay do not meet plan design parameters | 1 | $254.84 |
| Mail Brand Discount | Mail Brand Discount | Price adjudicated is significantly above the contracted category pricing | 2 | $266.28 |
| DAW6 Disallowed | DAW6 Disallowed | Brand dispensed; Company pay and/or copay do not meet plan design parameters | 2 | $25.07 |
| Zero Balance | | Price adjudicated is significantly above the contracted | | |

Fig. 6

Summary Of Charges

| Drug Category | Pharmacy Type | No. of Claims | Amount |
|---|---|---|---|
| Claim Return Adjustments | | | |
| Brand | Retail | 174 | ($45,446.44) |
| Generic | Retail | 798 | ($76,139.71) |
| Brand | Mail | 0 | $0.00 |
| Generic | Mail | 0 | $0.00 |
| Specialty | Retail | 11 | ($25,229.42) |
| Specialty | Mail | 0 | $0.00 |

Fig. 9

Summary Of Charges

| Drug Category | Pharmacy Type | No. of Claims | Amount |
|---|---|---|---|
| Manual/Paper Claims | | | |
| Brand | | 1 | $159.06 |
| Generic | | 2 | $12.60 |
| Totals | | 3 | $177.66 |
| All Claims | | | |
| Sales Tax | | | $542.17 |
| Totals | | 29,315 | $2,834,182.37 |

METHOD AND SYSTEM FOR MONITORING PRESCRIPTION DRUG DATA AND DETERMINING CLAIM DATA ACCURACY

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to analyzing prescription data, and in particular, monitoring pharmacy benefit managers' billing trends to identify areas of cost containment and potential pharmacy trends that may need to be addressed.

Description of the Related Art

Pharmacy claims have been billed without review, by the payer or fiduciary of the payer (broker, agent, or principal) prior to payment since the inception of pharmacy benefit management (PBM) services. The volume of prescription claims, the lack of transparency in pricing, confusing contract terms or definitions and the unfamiliar categorizations of medication therapy, make analysis of pharmacy claims complicated and slow.

Errors were not apparent to plan sponsors due to the volume of claims needing analysis and the delay in time for PBMs to perform their own reconciliation to identify errors in billing. Typically, the reconciliation process is performed months after the close of a contract year. Errors were usually discovered during annual audits by consultants or accounting firms. These audits are typically conducted on a representative sample of prescription claims, months after the close of a contract year with the PBM. Plan sponsors pay these auditing firms significant fees while waiting months for the completion of the process. The process of receiving, analyzing, seeking PBM clarification and producing the final audit findings occurs well after payment for the claims, making recovery of funds for material errors difficult. PBMs may chose a legal approach to settling audit recovery claims, which can lead to additional costs and time delays. A settlement may be significantly in favor of the PBM due to the lack of transparency, the audit process itself, and the resultant audit fatigue which is not the primary business of the payer.

Previously, pharmacy costs were such a small percentage of overall medical expenditures that potential the errors were ignored. Today however, with pharmacy representing 20-25% of medical costs and growing faster than some medical expenses, the potential savings are significant.

SUMMARY OF THE INVENTION

The present invention provides a method and system for scanning claims data. According to one embodiment, the method comprises receiving, by a computing system, contract details and claims, receiving, by the computer system, prescription transactions data associated with the claims, parsing, by the computer system, the transactions data into column values, and executing, by the computer system, analytics on the parsed transactions. Although the invention(s) in the present application are discussed by way of example with respect to pharmacy benefits, it is understood that the methods and systems described herein are applicable to other benefits, including benefits provided under health and/or dental plans. The analytics include comparing the parsed transactions against the contract details for accurate pricing, fees, and accepted treatment protocols concerning dose and quantity, comparing the parsed transactions with independent pricing data that is based on third-party pricing data and drug information, identifying material errors in the parsed transactions, determining withholdings from payment of the claims for a portion above a tolerance level based on the identified material errors. In at least one embodiment, the computer system creates tolerance levels based on current market intelligence, historical data inputs, projected outputs, to create an expected tolerance level. The method further comprising presenting, by the computer system, results of the execution of the analytics to a portal.

The method may further comprise receiving the prescription transactions data from a pharmacy benefit manager (PBM) or pharmacy computer. The prescription transactions data may be received through an application programming interface (API), Web interface, or a Secure File Transfer Protocol (SFTP) server interface. The prescription transactions data may be received in files or data communications through an API or Web interface. The contract details may include contract pricing terms and definitions, benefit design requirements, contracted administrative charges, and excluded categories of claims. Parsing the transactions may further comprise extracting and organizing data in the transactions data into data fields.

The material errors may include at least one of: claims price significantly above the contracted aggregate discount guarantee for a drug's class and source, claims with dispense as written codes (DAW) that are not allowed for brand medications (a price of the generic medication may be calculated and the amount over the plan sponsor's portion of the generic price may be withheld), claims with dispensing fees significantly above contracted terms, claims with incorrect administrative and clinical fees, claims with quantities or days' supply values above the benefit design's limitations with no prior authorization approvals, incorrect billing for company pay and copayment amounts, non-formulary medications dispensed with no prior authorizations, miscategorization of medications with resultant incorrect pricing applied, and claims billed incorrectly to the payer when a different payer is the primary. The method may further include determining the tolerance level based on an analysis of prescription data from a previous year and trending and statistical analysis of third-party pricing data and drug information. The portion may be an entire claim cost that is over contract terms calculations and acceptable variances. The tolerance level may be dynamically adjusted based on PBM performance. In one embodiment, the tolerance level is dynamically adjusted based on criteria selected from the group consisting of: retail brand and generic pricing discounts, retail specialty pricing discount, mail brand and generic pricing discounts, specialty pharmacy pricing discount, dispensing fees for retail, mail and specialty prescriptions, and pricing discounts for brand and generic zero balance due prescriptions. Parsing the transactions data may further comprise parsing the transactions data using a file format definition to map the transactions data into the column values.

The portal may include a claims scan module that causes monitoring of the claims according to claim contractual accuracy and a comparison of the claims to invoices from a PBM. The claims scan module may also cause generating of a post invoice/prepayment analysis of the claims to identify potential issues for correction prior to a payment of the claims. In another embodiment, the portal includes a claims scan module that causes analysis of the claims based on at least one of: pricing, package size errors, days' supply, patient eligibility, formulary adherence, prior authorizations, DEA scheduled medication rules, DAW codes, drug categorization, plan design rule, administrative fees, and dispensing fees. The claims scan module may cause generating of billing cycle summary, claims scan summary, review overview, detailed claims reporting and withhold payment overview. Additionally, claim scan reports may be generated including a claim scan overview report, claim scan-withhold payment claims detail: portal view, claim scan-withhold payment claims detail: excel output, and claim scan billing cycle summary report. The portal may include an ongoing monitoring module that causes generating of dashboards and reports that identify opportunities in the claims to save money or improve care. The ongoing monitoring module may also cause monitoring of medication utilization and trends, comparing pricing to a bench market price, identifying opportunities for therapeutic alternatives, dangerous drug combinations, and measuring PBM adherence to contracted pricing terms. The portal may also include a care insight application that causes monitoring of physician visits, hospital admissions, patient diagnosis and treatment history, and prescription compliance and history.

According to one embodiment, the system comprises a processor, and a memory having executable instructions stored thereon that when executed by the processor cause the processor to receive contract details associated with claims, receive prescription transactions data associated with the claims, parse the transactions data into column values, execute analytics on the parsed transactions, wherein the analytics include the processor to compare the parsed transactions against the contract details for accurate pricing, fees, and accepted treatment protocols concerning dose and quantity, compare the parsed transactions with independent pricing data that is based on third-party pricing data and drug information, identify material errors in the parsed transactions, and determine withholdings from payment of the claims for a portion above a tolerance level based on the identified material errors. The system further comprises the processor present results of the execution of the analytics to a portal.

BRIEF DESCRIPTION OF THE DRAWINGS

The invention is illustrated in the figures of the accompanying drawings which are meant to be exemplary and not limiting, in which like references are intended to refer to like or corresponding parts.

FIG. 6 illustrates an exemplary claims scan overview PDF report according to an embodiment of the present invention.

FIGS. 8 through 10 illustrate exemplary summary of charges interfaces according to an embodiment of the present invention.

FIG. 14 illustrates a claims insight detail report according to an embodiment of the present invention.

FIG. 15 illustrates an exemplary summary view of a claims scan overview report according to an embodiment of the present invention.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

The present disclosure includes a system with a claim scan feature that can review claims data efficiently and allows the pharmacy plan sponsor to review billed claims and associated errors, post adjudication and prepayment. The claim scan feature can eliminate, or significantly reduce, the need for a detailed annual or bi-annual audit, which is currently the industry standard. With the claim scan feature, material errors can be identified and withheld from the payment cycles throughout the year. The system may receive, process and analyze claims and billing data and apply all the variables, definitions, and myriad of contract terms, plan benefit design and payment terms to enables the claim scan feature to identify and report material errors in PBM billing prior to payment.

Figure 1:
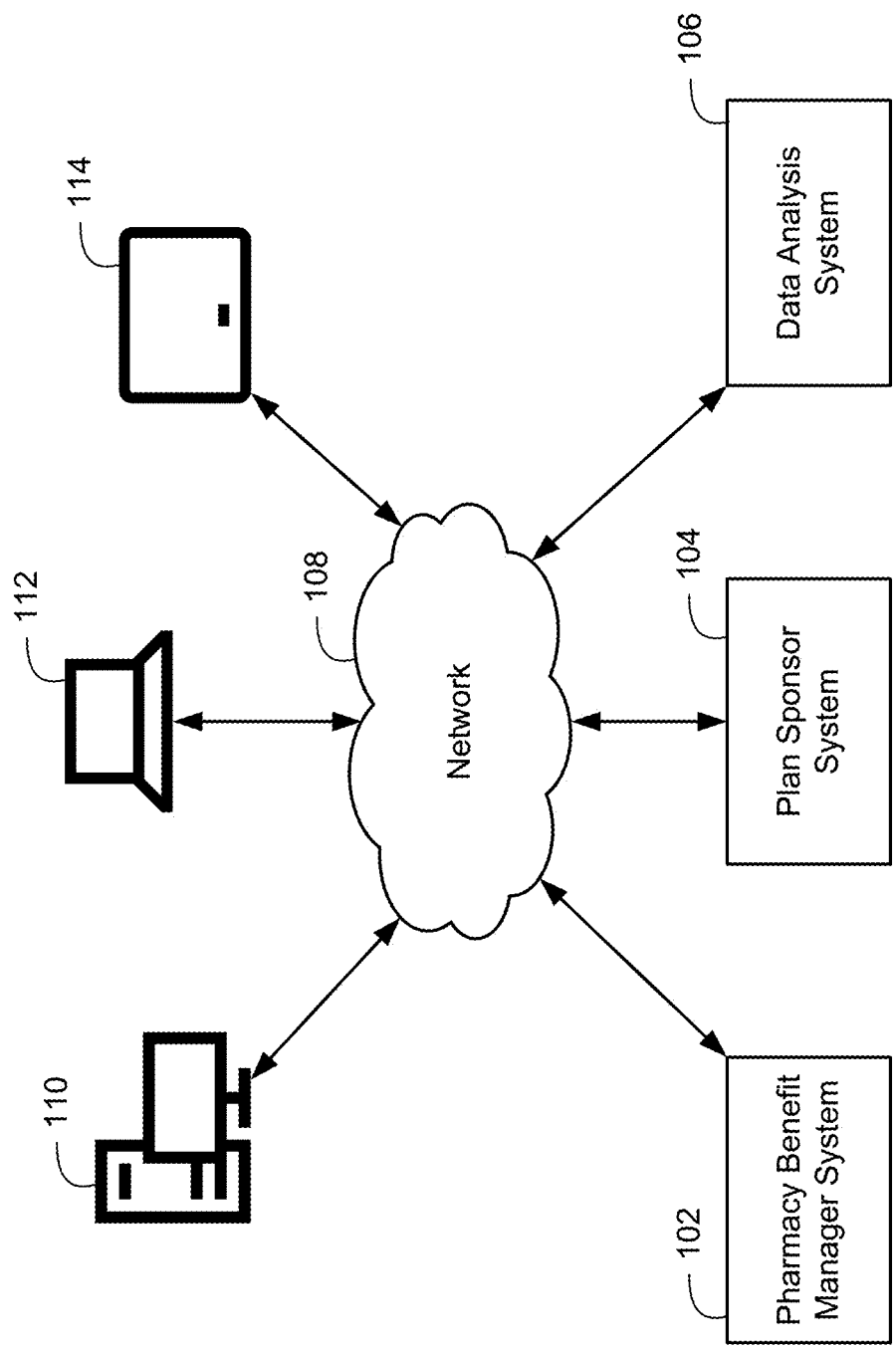
FIG. 1 illustrates a computing system according to an embodiment of the present invention.

FIG. 1 presents a computing system according to an embodiment of the present invention. The system presented in FIG. 1 includes a pharmacy benefit manager (PBM) system 102, plan sponsor system 104, a data analysis system 106, a network 108, a computer 110, a laptop 112, and a tablet 114. Pharmacy locations may use client computing devices, such as computer 110, laptop 112, and tablet 114 to communicate with PBM system 102 via network 108. A client computing device may comprise any device including a central processing unit and memory unit capable of connecting to a network. The pharmacy locations may contract with PBM system 102 on prices for various drugs. Computer 110, laptop 112, and tablet 114 may be a part of a pharmacy chain that owns or is associated with multiple locations. For example, large pharmacy chains like CVS, Walgreens, Rite-Aid, etc., have multiple retail locations. In such case, the pharmacy chain contracts with the PBM system 102 for drug prices, and the locations of the pharmacy chain can use the prices under the contract.

Network 108 may be any suitable type of network allowing transport of data communications across thereof. The network 108 may couple devices so that communications may be exchanged, such as between servers and client devices or other types of devices, including between wireless devices coupled via a wireless network, for example. A network may also include mass storage, such as network attached storage (NAS), a storage area network (SAN), cloud computing and storage, or other forms of computer or machine-readable media, for example. In one embodiment, the network may be the Internet, following known Internet protocols for data communication, or any other communication network, e.g., any local area network (LAN) or wide area network (WAN) connection, cellular network, wire-line type connections, wireless type connections, or any combination thereof. Communications and content stored and/or transmitted to and from client devices may be encrypted using, for example, the Advanced Encryption Standard (AES) with a 128, 192, or 256-bit key size, or any other encryption standard known in the art.

PBM system 102 may administer and/or process claims data related to payment requests for reimbursement of drugs (e.g., prescription drugs) rendered to a patient. The PBM system 102 may negotiate with one or more pharmacies regarding prices for various drugs (e.g., under a contract or agreement with a pharmacy). For example, PBM system 102 and a pharmacy can form an agreement on how much the plan sponsor 104 will compensate the pharmacy for certain drugs, although the amount charged by the PBM may be different from the amount paid to the pharmacy. PBM system 102 may also administer and processes claims data associated with a health insurance plan. For example, a PBM system 102 and a pharmacy determines under an agreement what the price for a particular drug will be for a health plan. The members of the health plan are charged a certain price for the drug based on the benefit design of the plan sponsor and administered by the PBM. The PBM system 102 communicates this plan design to the pharmacy.

The pharmacy computer 110, laptop 112, or tablet 114 may submit claims data to the PBM system 102 which forwards the adjudicated claims to the plan sponsor system 104 for approval and payment. Plan sponsor system 104 in hand may forward the claims data to data analysis system 106 for processing. Data analysis system 106 may communicate with a plurality of PBMs, such as PBM system 102, to obtain information relating to prices of various drugs. Data analysis system 106 can use the information to analyze transactions in the claims data against contract terms, benefit design, pricing accuracy, fees and accepted treatment protocols concerning dose and quantity. A hierarchy of rules and algorithms may also be used by data analysis system 106 to identify and categorize material errors in the transactions. A portion of the claims data with identified errors may be calculated and flagged to be withheld to the PBM system 102.

Figure 2:
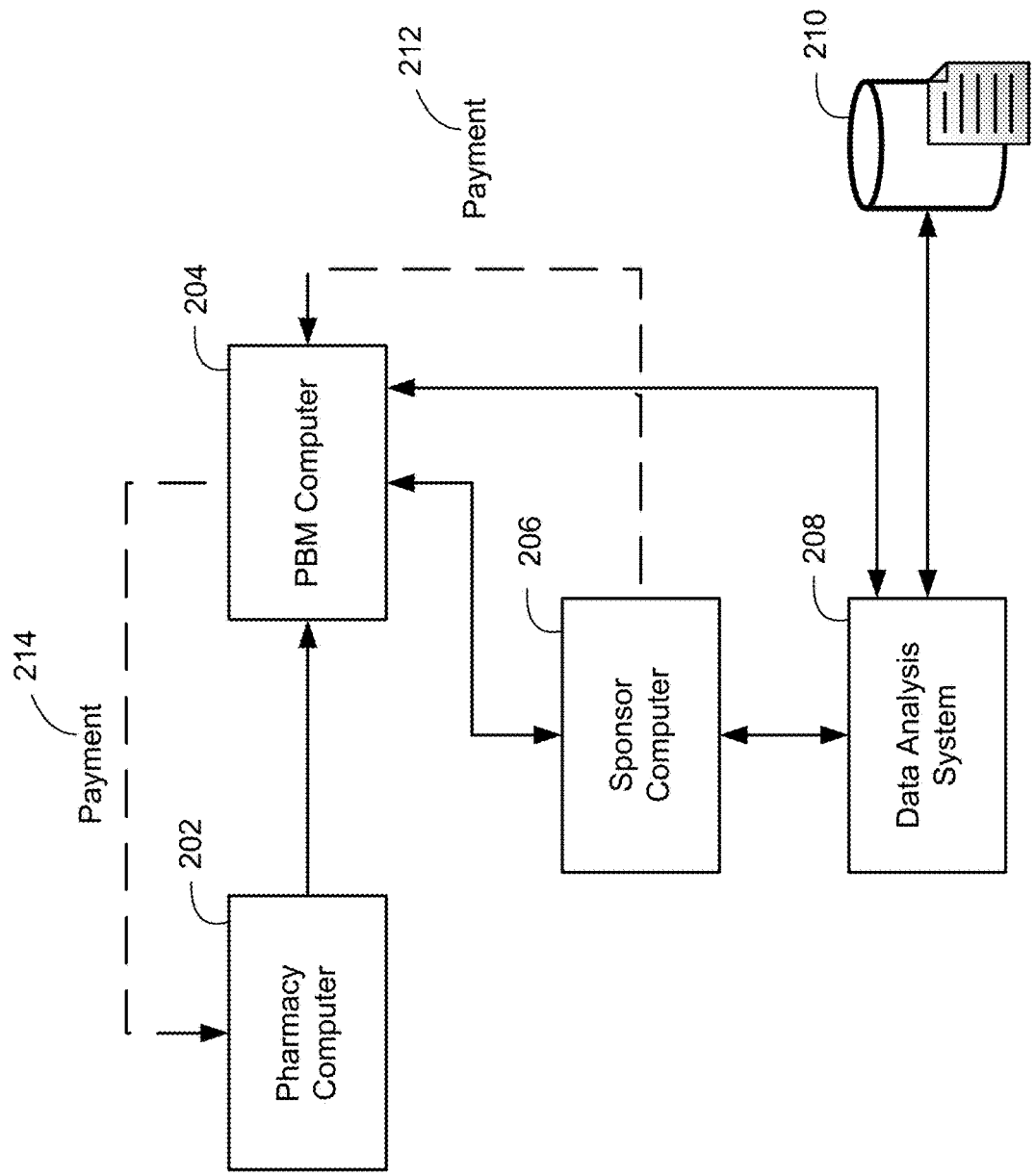
FIG. 2 illustrates a communication flow diagram of the computing system according to an embodiment of the present invention.

FIG. 2 presents a communication flow diagram of the computing system according to an embodiment of the present invention. Pharmacy computer 202 may transmit drug prescription claims data to PBM computer 204. PBM computer 204 may aggregate the prescription claims data and submit them to sponsor computer 206. The claims data may be received by sponsor computer 206 in real-time or batch through either an application programming interface (API) or files presented to a Secure File Transfer Protocol (SFTP) server. The claims data may include entries for a payment request along with drug pricing, drug quantity or supply, patient eligibility, formulary adherence, prior authorizations, Drug Enforcement Agency (DEA) scheduled medication rules, dispense as written (DAW) codes, drug categorization, insurance information, etc.

Data analysis system 208 may be used by sponsor computer 206 to analyze the information in the claims data against information stored in database 210, such as contract terms, benefit design, pricing accuracy, fees and accepted treatment protocols concerning dose and quantity. Database 210 may include prices of various drugs and drug information that have been collected from various sources. Analyzing the information may include identifying errors and determining pricing irregularities. An error or pricing irregularity may comprise, for example, an entry with a drug price that is beyond a certain tolerance for a particular drug, drug brand, or drug category. Entries including errors and pricing irregularities may be withheld from payment. The requested payment may be corrected by the data analysis system 208 and any withholdings may be reported. Sponsor computer 206 may authorize payment 212 to PBM computer 204 based on the corrected payment. PBM computer 204 may subsequently transfer a payment 214 to pharmacy computer 204.

Figure 3:
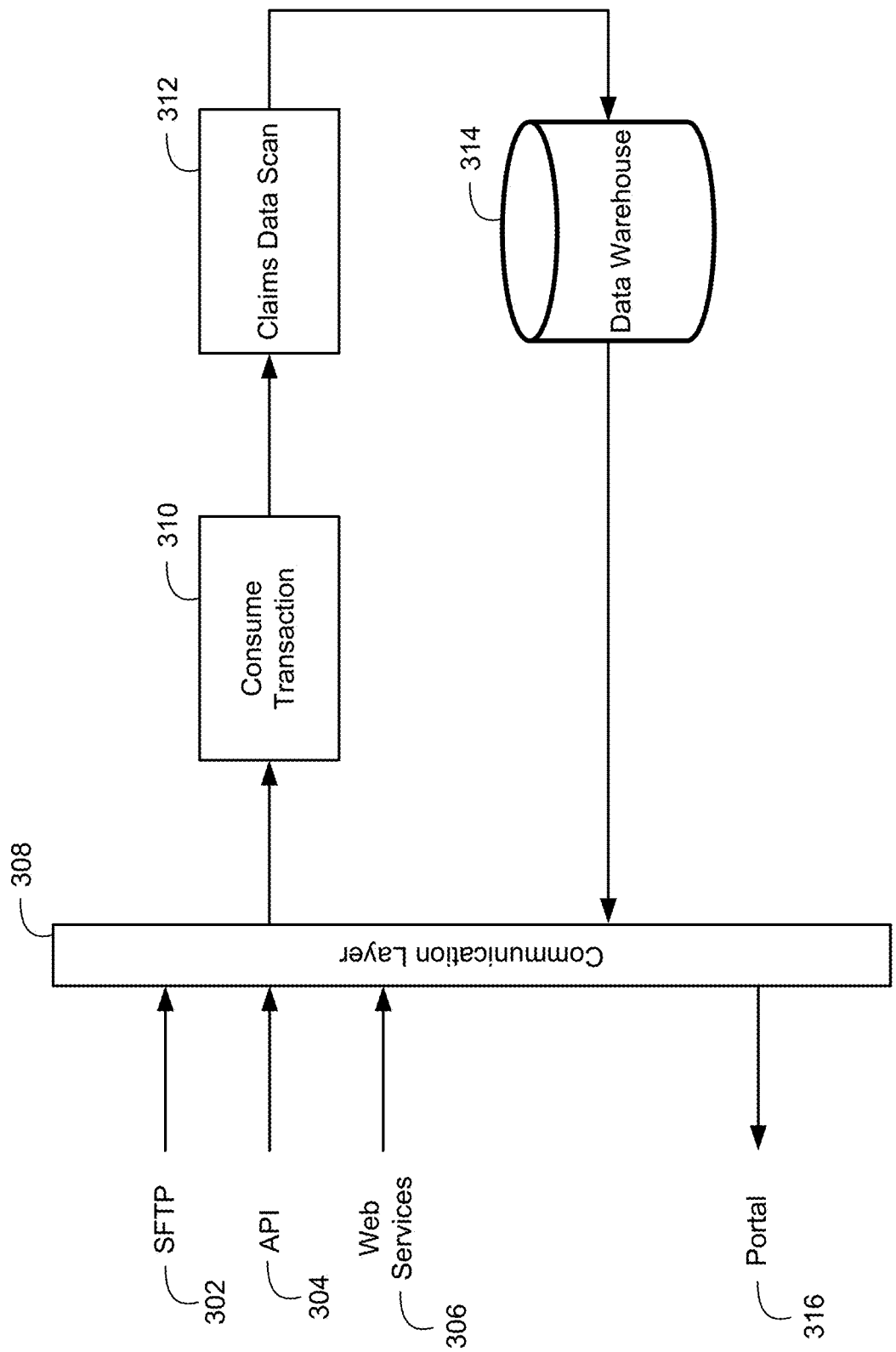
FIG. 3 illustrates a dataflow diagram of a data analysis system according to an embodiment of the present invention.

FIG. 3 presents a dataflow diagram of a data analysis system according to an embodiment of the present invention. Claims data may be processed by a data analysis system to identify errors and anomalies in billing and prices submitted by PBMs or pharmacies. Computing devices (e.g., of the plan sponsor) may access the data analysis system via communication layer 308 using SFTP 302, API 304, or Web services 306. The computing devices may include desktop computers, terminals, laptops, personal digital assistants (PDA), cellular phones, smartphones, tablet computers, or servers.

A client profile is created or retrieved to be used in analyzing the accuracy of a given pharmacy's submission of claims data. The client profile may include contract elements, such as contract terms and plan design elements corresponding to the pharmacy and PBM. Such information can be used by a process that loads and prepare data for reporting of transactions. Claims data may be transmitted to the data analysis system in files of a format specified from the computing device, such as comma-separated values (CSV) files. The files may be received in a transaction (310). A file format definition may be loaded as an available source-file map to parse and format the incoming data. The file format definition may include, for example, column position, column length, column format, and column name.

Claims data in the file can be loaded into the data analysis system and parsed using the column position and name in the definition.

The claims data may be processed in a claims data scan (312). The claims data scan 312 may run an analytics engine to generate metrics or analytics based on the claims data and compare the claims data with various third-party pricing data and drug information sources made available from data warehouse 314. The claims data and analytics generated from the analytics engine may be stored to the data warehouse 314 and made available to portal 316. Portal 316 may provide reporting of claims and analytic results from the analytics engine.

Figure 4:
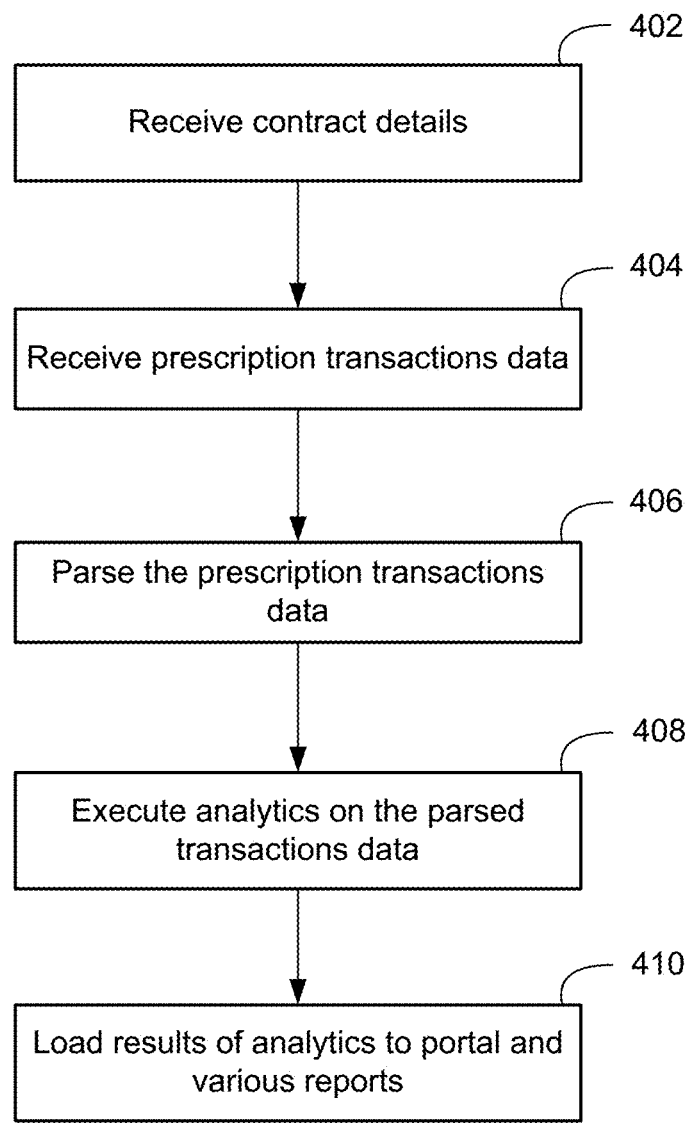
FIG. 4 illustrates a flowchart of a method for scanning claims data according to an embodiment of the present invention.

FIG. 4 presents a flowchart of a method for scanning claims data according to an embodiment of the present invention. A computing system may analyze claims data received from PBM or pharmacy computers, or any other data provider or data warehouse, including insurer computers, etc. The computing system may be accessed by the PBM or pharmacy computer through an application (e.g., using an API), Web interface, or a SFTP server interface. Contract details are received by a computing system, step 402. A contract input or selection may be received from the PBM or pharmacy computer to provide contract details for claims data associated with a PBM, pharmacy or pharmacy network. The contract details may include contract pricing terms and definitions, benefit design requirements, contracted administrative charges, and any excluded categories of claims. The contract details may be applied against transaction claims. The contract details can be applied consistently across the transactions of claims pertaining to a given pharmacy to identify errors or anomalies.

The computing system receives prescription transactions data of a claim from the PBM or pharmacy computer, step 404. The prescription transactions data may be transmitted in files or data communications through API or Web interface. The transactions data are parsed by the computing system into individual column values, step 406. Parsing the transactions data may include extracting and organizing specific data in the transactions data into data fields or a format suitable for processing. A file format definition may also be loaded for mapping transmitted files into a suitable format for the computing system. The file format definition may include column position, column length, column format, and column name. Claims data transmitted in files can be loaded into the data analysis system and parsed using, for example, the column position and column name in the definition.

Analytics are executed on the parsed transactions data, step 408. The parsed transactions data may be fed into a claims data scan engine. The claims data scan engine may analyze and compare the transactions data against the contract details for accurate pricing, fees, and accepted treatment protocols concerning dose and quantity. Additionally, the claims data scan engine may compare the transactions data with independent pricing data that may be generated or developed based on third-party pricing data and drug information using, for example, machine-learning and trend analysis.

Executing the analytics may further include applying a hierarchy of rules and algorithms to the transactions data to identify and categorize material errors. The identified errors for specific claims, e.g., during a specified billing cycle, may cause dollar amounts to be withheld from a payment for an excess portion above a tolerance level. Some potential errors that can result in the withholding of dollars from payment of a claim may include: claims price significantly above the contracted aggregate discount guarantee for a drug's class and source, claims with dispense as written codes (DAW) that are not allowed for brand medications (a price of the generic medication may be calculated and the amount over the plan sponsor's portion of the generic price may be withheld), claims with dispensing fees significantly above contracted terms, claims with incorrect administrative and clinical fees, claims with quantities or days' supply values above the benefit design's limitations with no prior authorization approvals, incorrect billing for company pay and copayment amounts, non-formulary medications dispensed with no prior authorizations, miscategorization of medications with resultant incorrect pricing applied, and claims billed incorrectly to the payer when a different payer is the primary.

The claims data scan engine may determine a tolerance level setting for identifying claims that are significantly outside of contracted pricing terms or plan benefit design, and calculate a value to withhold from payment of the claim. The rules and algorithms can also be applied to the transactions data to calculate a portion of the claims to be withheld. The portion may be of an entire claim cost that is over contract terms calculations and acceptable variances. Categories of findings that are most valuable and easiest to defend for the plan sponsor can also be determined.

Establishing a tolerance level allows for market variability in pricing and other factors for a plurality of different medications. The tolerance level may be established by one or more algorithms using factors based on findings in an initial summary analysis of prescription data from the previous year and taking trending and statistical analysis third-party pricing data and drug information to create the tolerance level. The level of variance from contracted guarantees and terms may be used to set initial factors used in the calculation of tolerance levels. Additionally, the tolerance level may account for and accommodate aggregate discount terms commonly used in PBM contracts for pricing guarantees. The tolerance levels for pricing discounts and dispensing fees may be dynamically adjusted throughout the year based on PBM performance. Dynamic calculations may be adjusted based on the goal of having a net balance of zero owed from the PBM to the plan at the end of the year, when netted against pricing discount guarantees. For example, the following criteria may be dynamically adjusted each quarter: retail brand and generic pricing tolerance points, retail specialty pricing tolerance point, mail brand and generic pricing tolerance points, specialty pharmacy pricing tolerance points, dispensing fees for retail, mail and specialty prescriptions, and pricing tolerance points for brand and generic zero balance due prescriptions.

Results of the analytics are loaded to a portal, step 410, or delivered directly to the client via API, Web service, or secure file transmission. The parsed transactions data and results of the analytics from the claims data scan engine may be retained in a data warehouse (or database) for retrieval by the portal. The results may be accessed through the portal, along with various reports supporting the results and suggestions for withholding payment for specific claims. The portal may provide access to prescription data. Particularly, the portal may allow a user to monitor post invoice/prepayment financial trends and analyze their prescription data on an on-going basis. The portal can deliver actionable data that can be viewed at varying levels of detail based on user-defined security levels. These various levels of detail may aid in identifying areas of cost containment and potential pharmacy trends that may need to be addressed. Data provided in the portal may allow a user to pinpoint problems, such as in pricing, drug utilization, provider performance, and pharmacy benefit manager billing.

According to one embodiment, the portal may include applications, such as claims insight, provider insight, and care insight. A claims insight application may include a claims scan module and an ongoing monitoring module. The claims scan module may provide monitoring of claims according to claim contractual accuracy and comparing the claims to invoices from a PBM. According to one embodiment, PBM performance may be monitored against user-defined key performance measurements in the claims scan module. The claims scan module may further generate a post invoice/prepayment analysis of pharmacy claims, so that any potential issues may be identified for correction prior to payment to the PBM. The claims scan module is described in further detail with respect to the description of FIGS. 5-16.

The ongoing monitoring module may generate dashboards and reports that enable the user to quickly identify opportunities in prescription claims data to save money or improve care. The ongoing monitoring module is capable of monitoring medication utilization and trends, comparing pricing to a bench market price, identifying opportunities for therapeutic alternatives, dangerous drug combinations, and measuring PBM adherence to contracted pricing terms.

A provider insight application may provide the ability to monitor provider prescribing patterns and study these patterns at various levels of detail and categorization. Provider analysis can be done based on patient groups, geography, practice, practice specialty or individual prescriber.

A care insight application may allow the user to monitor physician visits, hospital admissions, patient diagnosis and treatment history, and prescription compliance and history. By using both prescription and medical data on the same platform, care managers can prioritize their workload to care for the patients in a strategic manner. Care insight data can be viewed from a general population level down to the individual patient level.

Claims scan module is operable to generate a per billing cycle report including post invoice/prepayment analysis of pharmacy claims. Material errors may be identified and addressed prior to payment to the PBM. Claims scan may analyze critical areas including: pricing, package size errors, days' supply, patient eligibility, formulary adherence, prior authorizations, DEA scheduled medication rules, DAW codes, drug categorization, plan design rule, administrative fees, and dispensing fees. Errors and alerts displayed within the claims scan module can be customizable by the user. The user may establish their own set of categories, rules, and factors in claims scan rules.

In one embodiment, the claims scan module includes billing cycle summary, claims scan summary, review overview, detailed claims reporting and withhold payment overview. Additionally, claim scan reports may be generated including a claim scan overview report, claim scan-withhold payment claims detail: portal view, claim scan-withhold payment claims detail: excel output, and claim scan billing cycle summary report.

Figure 5:
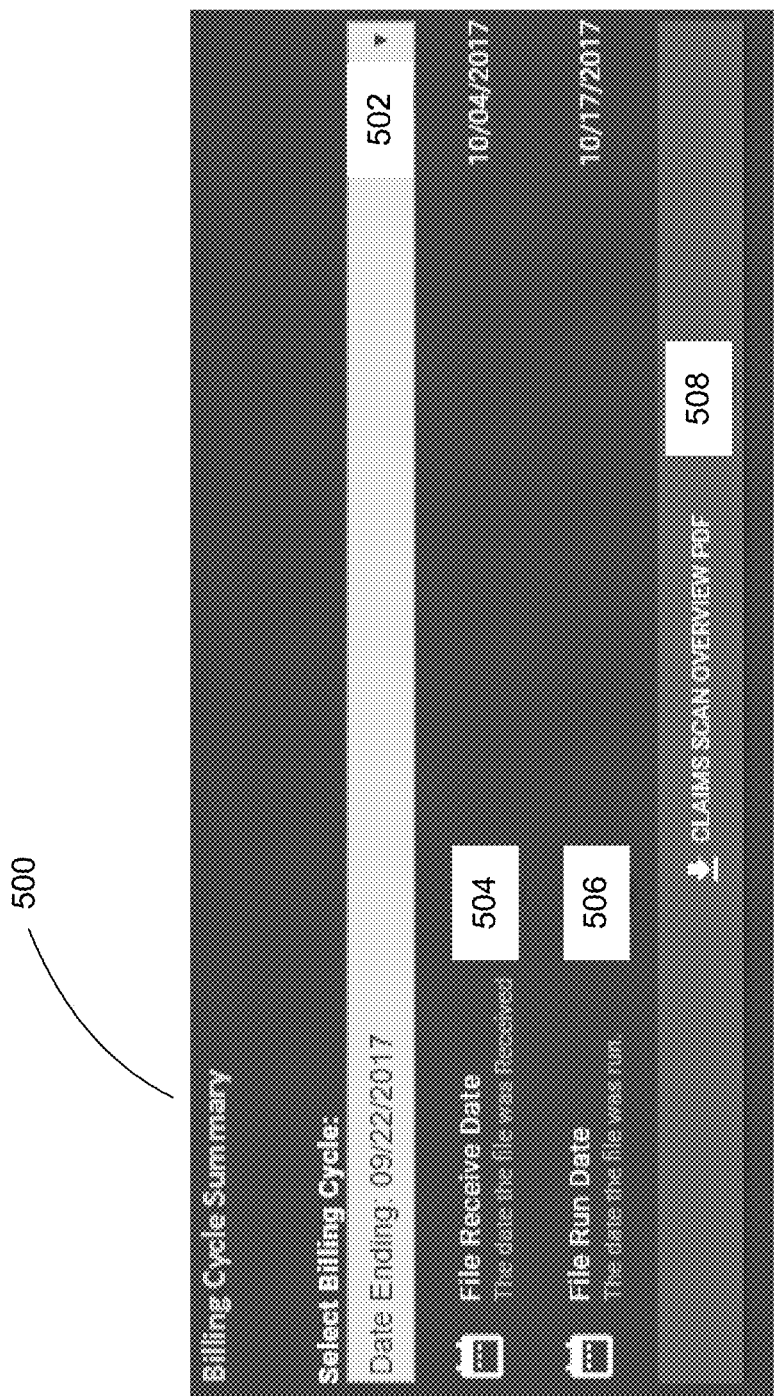
FIG. 5 illustrates an exemplary billing cycle summary interface according to an embodiment of the present invention.

FIG. 5 presents an exemplary billing cycle summary interface according to an embodiment of the present invention. Billing cycle summary interface 500 includes a billing cycle dropdown 502. A PBM's billing cycles may be selected from a list of available ending dates in the billing cycle dropdown 502. The billing cycle summary interface further includes file receive data 504 and file run date 506. File receive date 504 displays the date the data file was received from the PBM. The file run date 506 displays the date the file was loaded into for analysis. Claims scan overview PDF 508 may be selected to produce a claims scan overview report in portable document format (PDF).

FIG. 6 presents an exemplary claims scan overview PDF report according to an embodiment of the present invention. Claims with errors may be grouped within a withhold payment claims section of the report. The claims scan overview report may include a code column that categorizes the errors by contract terms, drug types and pharmacy source. The claims scan overview report may provide a categorized summary of the number of claims that should be reviewed or withheld from payment, grouped by reason rationale, and a dollar value for those claims with alerts or errors based on user-defined rules. A reason column may provide a brief explanation of the errors and a formula that was used to calculate the amount to withhold or review.

Figure 7:
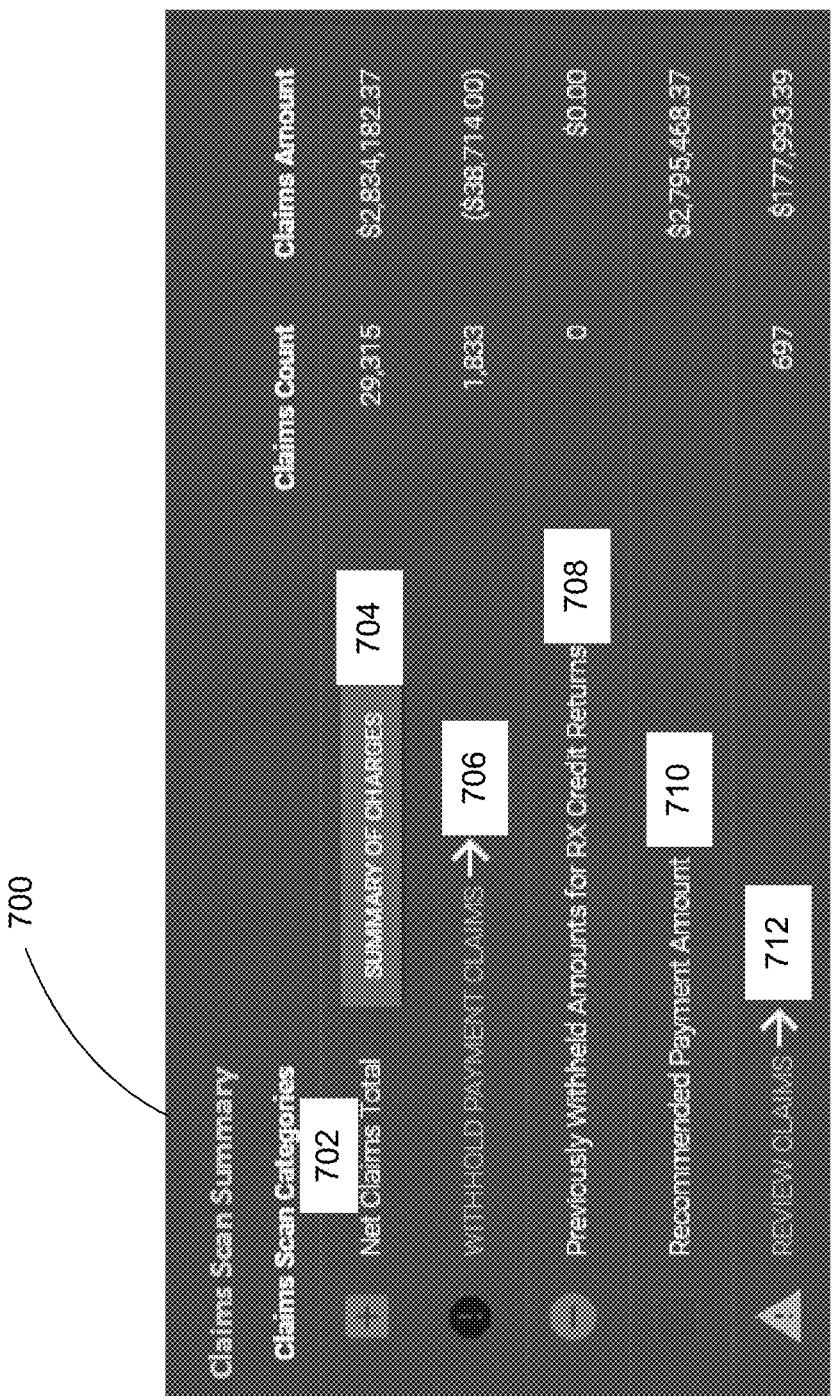
FIG. 7 illustrates an exemplary claims scan summary interface according to an embodiment of the present invention.
Figure 8:
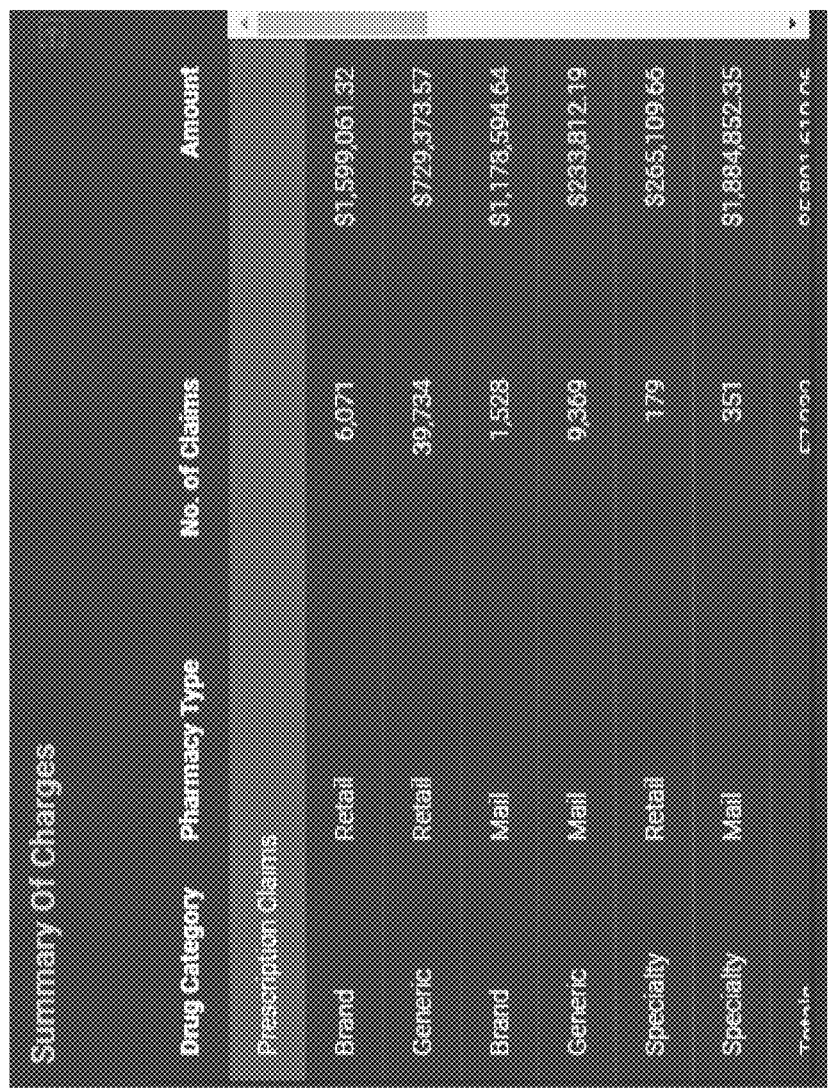

FIG. 7 presents an exemplary claims scan summary interface according to an embodiment of the present invention. The claims scan summary interface 700 may provide a high-level summary view of claims with links to additional claims detail. The claims scan summary interface includes a net claims total 702 that shows a total count and amount of prescription claims for a given time-period. To view more detail, the summary of charges 704 button may be selected to view the summary of claims count and the dollars associated with each drug category and pharmacy type, as illustrated in FIGS. 8-10. A summary of charges report may provide data on prescription claims (FIG. 8), credit return adjustments (FIG. 9), and manual/paper claims and sales tax (FIG. 10).

Referring back to FIG. 7, the claims scan summary interface 700 includes a withhold payment claims 706 that displays the claim count and amount of prescriptions for which payment should be withheld, based on the rules set forth by the client in the claims scan rules. A summary of the claims, grouped by the withhold reason, can be viewed by clicking on withhold payment claims 706. Previously withheld amounts for RX credit returns 708 may display the count and amount of any claims with previously withheld amounts that were reversed. These amounts may be credited against a current withhold amount. Recommended Payment Amount 710 may display the total recommended payment amount for the claims in the selected billing cycle. Review claims 712 may display the count and amounts of claims recommended to be reviewed with the PBM, but not withheld from the payment amount. A summary of the claims, grouped by the review reason, can be viewed by clicking on review claims 712.

Figure 11:
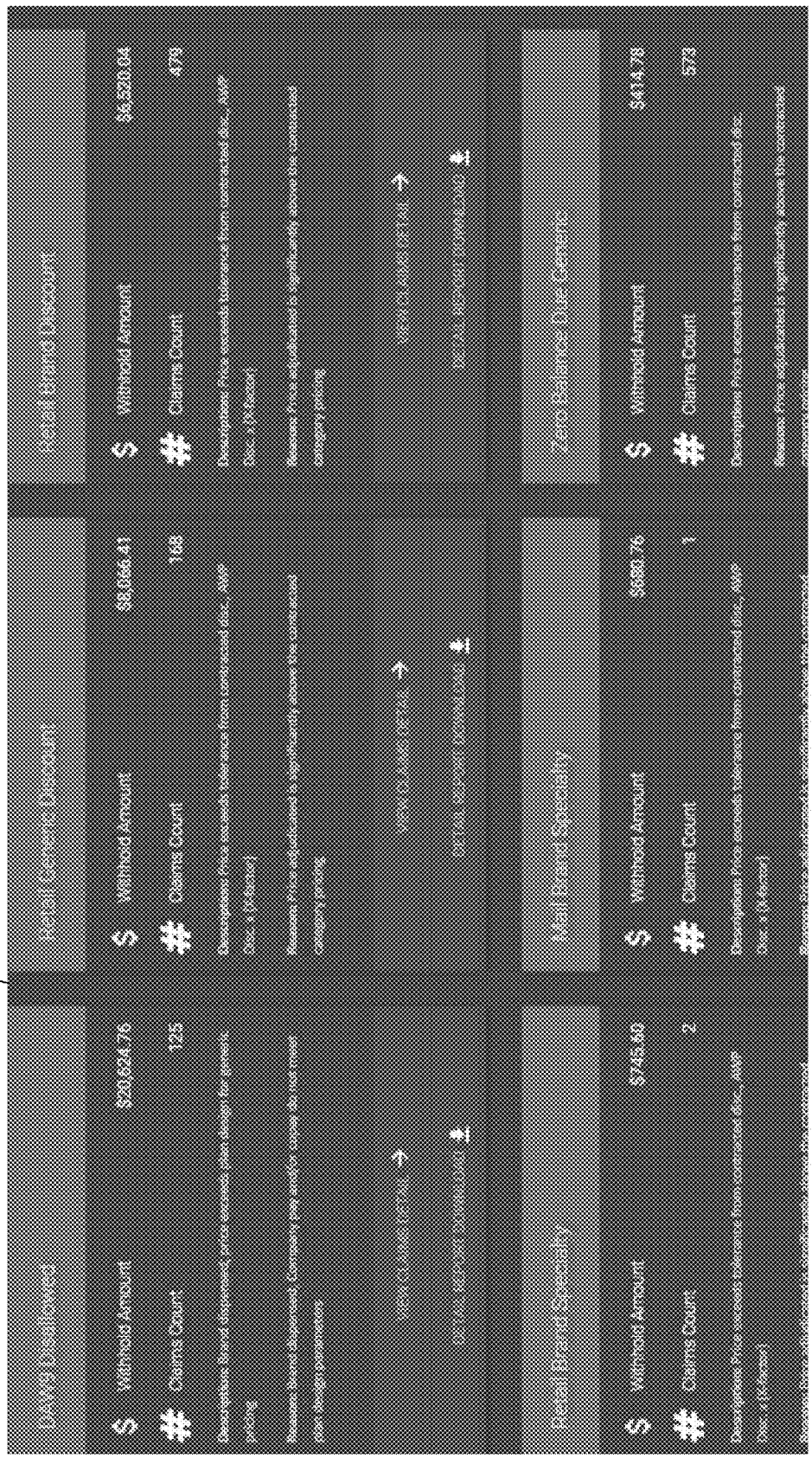
FIGS. 11 and 12 illustrate a withhold/review payment claims report according to an embodiment of the present invention.
Figure 12:
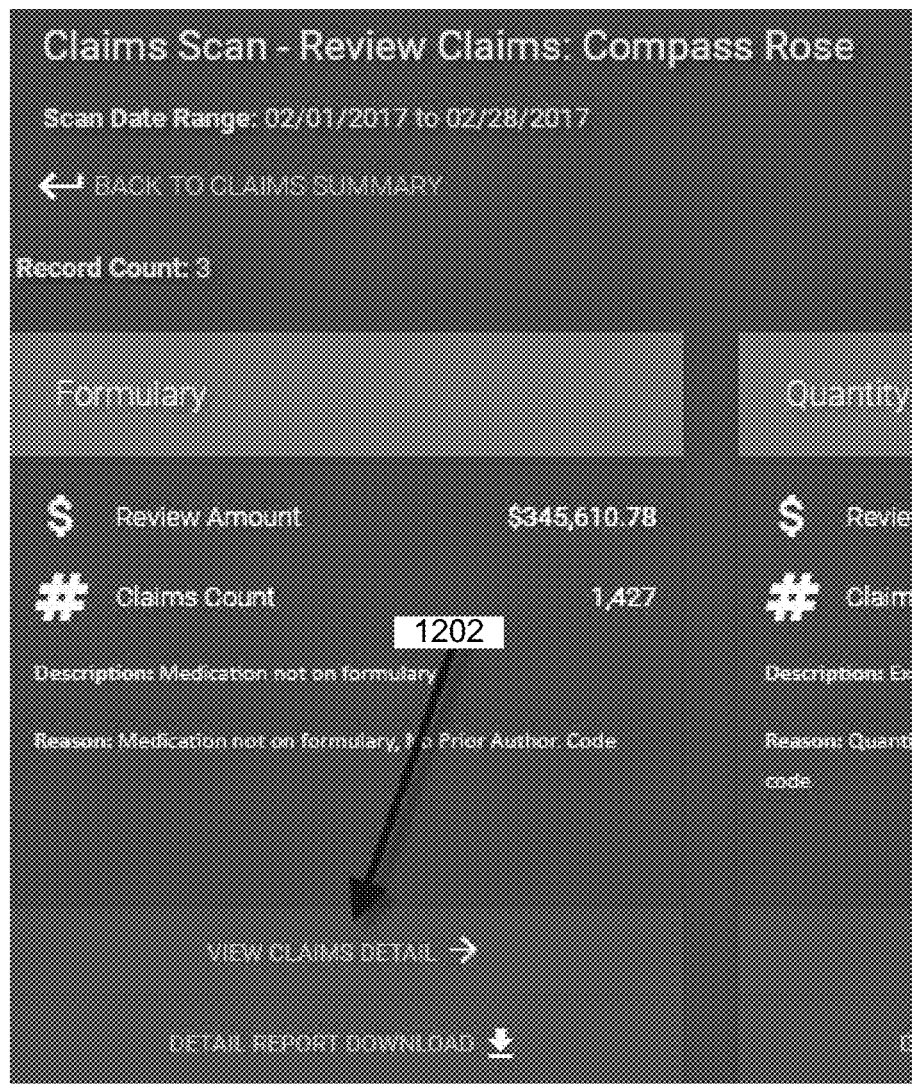

Withhold payment claims 706 or review claims 712, may be selected to generate a withhold/review payment claims report, as illustrated in FIG. 11. Values in the withhold/review payment claims report 1100 may be grouped by alert category and include information, such as a withhold amount and a claims count. The withhold amount may indicate a total amount to withhold from payment for the claims in the alert category. The claims count may indicate the total number of claims in the alert category. From the withhold/review payment claims report, a user may view or download additional claim-level detail by clicking on view claims detail 1202, as illustrated in FIG. 12.

Figure 13:
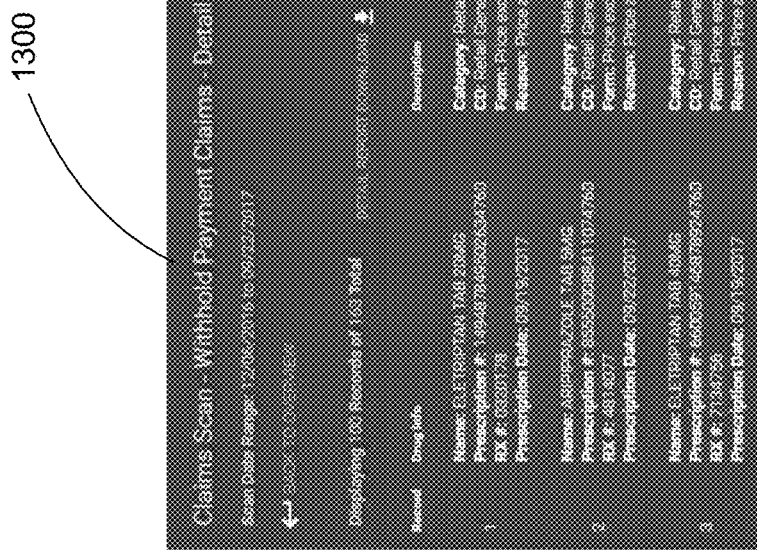
FIG. 13 illustrates an exemplary claims detail report according to an embodiment of the present invention.

FIG. 13 presents an exemplary claims detail report according to an embodiment of the present invention. The claims detail report 1300 includes details on the drug including a description for an alert, fees, contracted price, and amount withheld. The metrics reported on the claims detail report 1300 may include company, copay, dispensing, contracted prices, and withhold amount. Company may indicate the total dollar amount billed to the company. Copay may indicate the total amount paid by the patient. Dispensing may indicate the amount paid for the dispensing fee. Contracted prices may indicate the calculated prices based on the contractual price between Client and PBM. Withhold amount may indicate the amount to be withheld from the payment due to the error/reason for the alert.

To view claim-level detail, a detail report download link may be selected, for example, from within the withhold/review payment claims detail report 1100 or the claims detail report 1300 to produce a claims insight detail report 1400, illustrated in FIG. 14. Claims insight detail report 1400 may provide claim-level detail for claims recommended for review prior to making payment. The metrics reported for each claim in claims insight detail report 1400 may be calculated based on: quantity, average wholesale price (AWP) unit price, unit price paid company pay, copay, dispensing fee, admin fee, withhold amount, and description of criteria. The quantity may refer to the number of units in the prescriptions claim. AWP unit price may refer to the average wholesale price for one unit of the medication. Unit price paid may refer to the unit price paid (company pay+ copay) to the PBM. Company pay may refer to the total dollar amount paid by the company for the claim. Copay may refer to the total amount paid by the patient in copay. Dispensing fee may refer to the amount paid to the PBM/ pharmacy as a dispensing fee. Admin fee may refer to the administrative fee paid to the PBM for the claim. Withhold amount may refer to the amount to withhold from payment for the claim. Description of criteria may refer to the contract pricing terms and factor used to determine claims that significantly exceeded the contract guarantees.

Figure 15:
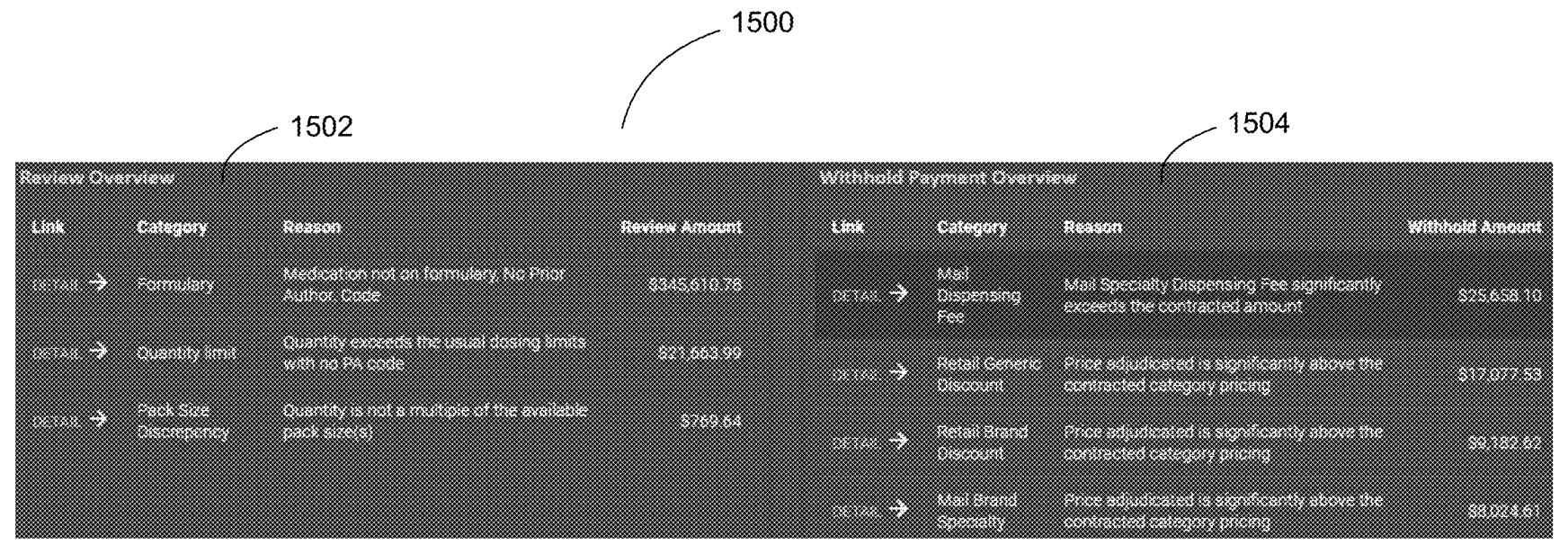

FIG. 15 presents an exemplary summary view of a claims scan overview report according to an embodiment of the present invention. Claims scan overview report 1500 may include a summary for claims to be reviewed (review overview 1502) and claims in which payment is recommended to be withheld (withhold payment overview 1504).

FIGS. 1 through 15 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer-readable program code) are stored in a main and/or secondary memory, and executed by one or more processors (controllers, or the like) to cause the one or more processors to perform the functions of the invention as described herein. In this document, the terms "machine readable medium," "computer-readable medium," "computer program medium," and "computer usable medium" are used to generally refer to media such as a random-access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A method, in a data processing system comprising a processor and a memory, for scanning claims data, the method comprising:
   receiving, by a computing system, contract details data associated with a pharmacy benefit manager system;
   receiving, by the computer system via electronic file or data communications from the pharmacy benefit manager system through a communication layer using an application programming interface, a web interface, or secure file transfer protocol, claims data including prescription transactions data aggregated by the pharmacy benefit manager system from a plurality pharmacy computers;
   parsing, by the computer system, the prescription transactions data from the electronic file or data communications into column values by extracting data from the prescription transaction data and organizing the extracted data into data fields based on a source-file map including a file format definition;
   executing, by the computer system, analytics on the parsed transactions data via a data analysis system, the analytics including the data analysis system:
      comparing the parsed transactions data against the contract details data that determines accurate pricing, fees, and adherence to accepted treatment protocols concerning dose and quantity;
      obtaining third-party pricing data and drug information from a database;

comparing the parsed transactions data with independent pricing data generated based on the third-party pricing data and drug information using machine-learning and trend analysis;

calculating metrics for claims in the parsed transactions data;

identifying material errors in the parsed transactions data based on the comparisons of the parsed transactions data with the contract details data using the independent pricing data;

determining a portion of individual claims above a tolerance level to withhold from payment of claims based on the identified material errors and user-defined rules;

dynamically adjusting the tolerance level based on performance of a pharmacy benefit manager (PBM); and storing, by the computer system, the determined portion to withhold from payment of claims, the parsed transaction data, and the material errors to a data warehouse;

loading, by the computer system, the determined portion to withhold from payment of claims, the parsed transactions data, and the material errors from the data warehouse to a portal user interface through the communication layer, the portal user interface including application modules that are accessible by a client device;

generating, by the application modules, reports based on the metrics and the material errors, the generated reports including a summary of given ones of the claims that should be reviewed or withheld from payment and alerts based on the user-defined rules;

monitoring and generating, by the application modules, analysis of medication utilization and trends, provider prescribing patterns, and medical care data associated with the parsed transactions data, the analysis rendered on the portal user interface at various levels of detail and categorization; and identifying, by the application modules, therapeutic alternatives and dangerous drug combinations based on the parsed transactions data.

2. The method of claim 1 wherein the contract details data include contract pricing terms and definitions, benefit design requirements, contracted administrative charges, and excluded categories of claims.

3. The method of claim 1 wherein the material errors include at least one of: claims price significantly above the contracted aggregate discount guarantee for a drug's class and source, claims with dispense as written codes (DAW) that are not allowed for brand medications, claims with dispensing fees significantly above contracted terms, claims with incorrect administrative and clinical fees, claims with quantities or days' supply values above the benefit design's limitations with no prior authorization approvals, incorrect billing for company pay and copayment amounts, non-formulary medications dispensed with no prior authorizations, miscategorization of medications with resultant incorrect pricing applied, and claims billed incorrectly to the payer when a different payer is the primary.

4. The method of claim 1 further comprising determining the tolerance level based on an analysis of prescription data from a previous year and trending and statistical analysis of third-party pricing data and drug information.

5. The method of claim 1 wherein the portion of individual claims includes a cost that is over contract terms calculations and acceptable variances.

6. The method of claim 1 further comprising dynamically adjusting the tolerance level based on criteria selected from the group consisting of: retail brand and generic pricing discounts, retail specialty pricing discount, mail brand and generic pricing discounts, specialty pharmacy pricing discount, dispensing fees for retail, mail and specialty prescriptions, and pricing discounts for brand and generic zero balance due prescriptions.

7. The method of claim 1 wherein the portal user interface includes a claims scan module that causes monitoring of the claims according to claim contractual accuracy and a comparison of the claims to invoices from a PBM.

8. The method of claim 1 wherein the portal user interface includes a claims scan module that causes generating of a post invoice/prepayment analysis of the claims to identify potential issues for correction prior to a payment of the claims.

9. The method of claim 1 wherein the portal user interface includes a claims scan module that causes analysis of the claims data based on at least one of: pricing, package size errors, days' supply, patient eligibility, formulary adherence, prior authorizations, DEA scheduled medication rules, DAW codes, drug categorization, plan design rule, administrative fees, and dispensing fees.

10. The method of claim 1 wherein the portal user interface includes a claims scan module that causes generating of billing cycle summary, claims scan summary, review overview, and withhold payment overview.

11. The method of claim 1 wherein the portal user interface includes an ongoing monitoring module that causes generating of dashboards and reports that identify opportunities in the claims data to save money or improve care.

12. The method of claim 11 wherein the ongoing monitoring module causes:

monitoring of medication utilization and trends;
comparing pricing to a bench market price;
identifying opportunities for therapeutic alternatives;
dangerous drug combinations; and
measuring PBM adherence to contracted pricing terms.

13. The method of claim 1 wherein the portal user interface includes a care insight application that causes monitoring of physician visits, hospital admissions, patient diagnosis and treatment history, and prescription compliance and history.

14. The method of claim 1 wherein executing the analytics on the parsed transactions data further comprises the analytics system:

comparing the parsed transactions data against the contract details data for adherence to plan benefit design and market price variability; and identifying material errors in the parsed transactions data based on the comparisons of the parsed transactions data with the plan benefit design and the market price variability using the independent pricing data.

15. A system for scanning claims data, the system comprising:

a processor; and
a memory having executable instructions stored thereon that when executed by the processor cause the processor to:

receive contract details data associated with a pharmacy benefit manager system;

receive, via electronic file or data communications from the pharmacy benefit manager system through a communication layer using an application programming interface, a web interface, or secure file transfer protocol, claims data including prescription transactions data aggregated by the pharmacy benefit manager system from a plurality pharmacy computers;

parse the prescription transactions data from the electronic file or data communications into column values by extracting data from the prescription transaction data and organizing the extracted data into data fields based on a source-file map including a file format definition;

execute analytics on the parsed transactions data via a data analysis system, the analytics including the processor to:

compare the parsed transactions data against the contract details data that determines accurate pricing, fees, and adherence to accepted treatment protocols concerning dose and quantity;

obtain third-party pricing data and drug information from a database;

compare the parsed transactions data with independent pricing data generated based on the third-party pricing data and drug information using machine-learning and trend analysis;

calculate metrics for claims in the parsed transactions data;

identify material errors in the parsed transactions data based on the comparisons of the parsed transactions data with the contract details data using the independent pricing data;

determine a portion of individual claims above a tolerance level to withhold from payment of claims based on the identified material errors and user-defined rules;

dynamically adjust the tolerance level based on performance of a pharmacy benefit manager (PBM); and store the determined portion to withhold from payment of claims, the parsed transaction data, and the material errors to a data warehouse;

load the determined portion to withhold from payment of claims, the parsed transactions data, and the material errors from the data warehouse to a portal user interface through the communication layer, the portal user interface including application modules that are accessible by a client device;

generate reports based on the metrics and the material errors, the generated reports including a summary of given ones of the claims that should be reviewed or withheld from payment and alerts based on the user-defined rules;

monitor and generate, via the application modules, analysis of medication utilization and trends, provider prescribing patterns, and medical care data associated with the parsed transactions data, the analysis rendered on the portal user interface at various levels of detail and categorization; and identify, via the application modules, therapeutic alternatives and dangerous drug combinations based on the parsed transactions data.

16. A system for improving efficiency and accuracy in processing of pharmacy claims, the system comprising:

a plan sponsor system communicatively coupled to a pharmacy benefit manager system that receives claims data from the pharmacy benefit manager system, the claims data including prescription transactions data aggregated by the pharmacy benefit manager system from a plurality of pharmacy computers;

a database storing third-party pricing data and drug data;

a data analysis system communicatively coupled to the plan sponsor system, the pharmacy benefit manager system, and the database, the data analysis system is configured to:

receive the claims data from the plan sponsor system through a communication layer using an application programming interface, a web interface, or secure file transfer protocol, the third-party pricing data and drug data from the pharmacy benefit manager system, and contract details data corresponding to the pharmacy benefit manager system and the plurality of pharmacy computers from the database;

parse the prescription transactions data into column values by organizing the claims data into data fields based on a source-file map including a file format definition;

compare the parsed prescription transactions data against the contract details data and independent pricing data generated based on the third-party pricing data and drug data using machine-learning and trend analysis;

determine accuracy of the parsed prescription transactions data in accordance with pricing, fees, and adherence to accepted treatment protocols concerning dose and quantity based on the comparison;

identify material errors in the parsed prescription transactions data based on the comparison;

determine a portion of individual claims above a tolerance level to withhold from payment of claims based on the identified material errors and user-defined rules;

dynamically adjust the tolerance level based on performance of a pharmacy benefit manager (PBM); and store the determined portion to withhold from payment of claims, the prescription transaction data, and the material errors to a data warehouse;

a portal user interface communicatively coupled to the data analysis system, the portal user interface loads the determined portion to withhold from payment of claims, the parsed prescription transactions data, and the material errors from the data warehouse through the communication layer, wherein the portal user interface is accessible by a client device; and application modules installed on the portal user interface, the application modules configured to:

generate reports based on the parsed prescription transactions data and the material errors, the reports including a summary of given ones of the claims that should be reviewed or withheld from payment and one or more alerts based on the user-defined rules, and monitor and generate analysis of medical care data associated with the parsed prescription transactions data, the analysis rendered on the portal user interface at various levels of detail and categorization.

17. The system of claim 16 wherein the contract details data include contract pricing terms and definitions, benefit design requirements, contracted administrative charges, and excluded categories of claims.

18. The system of claim 16 wherein the data analysis system is further configured to determine the tolerance level based on an analysis of prescription data from a previous year and trending and statistical analysis of the third-party pricing data and drug information.

19. The system of claim 16 wherein the data analysis system is further configured to:
compare the prescription parsed transactions data against the contract details data for adherence to plan benefit design and market price variability; and
identify material errors in the parsed transactions data based on the comparisons of the parsed prescription transactions data with the plan benefit design and the market price variability using the independent pricing data.

* * * * *